United States Patent
Wolff et al.

(10) Patent No.: US 6,818,647 B2
(45) Date of Patent: Nov. 16, 2004

(54) METHOD AND COMPOSITION FOR RESTORING DIURETIC AND RENAL FUNCTION

(75) Inventors: Andrew A. Wolff, San Francisco, CA (US); George F. Schreiner, Los Altos, CA (US)

(73) Assignee: CV Therapeutics, Inc, Palo Alto, CA (US)

( * ) Notice: Subject to any disclaimer, the term of this patent is extended or adjusted under 35 U.S.C. 154(b) by 0 days.

(21) Appl. No.: 10/150,501

(22) Filed: May 16, 2002

(65) Prior Publication Data

US 2003/0096810 A1 May 22, 2003

Related U.S. Application Data

(63) Continuation of application No. 09/861,873, filed on May 21, 2001, now abandoned, which is a continuation of application No. 09/470,068, filed on Dec. 22, 1999, now abandoned, which is a continuation of application No. PCT/US99/08879, filed on Apr. 23, 1999.

(60) Provisional application No. 60/083,638, filed on Apr. 30, 1998, and provisional application No. 60/083,022, filed on Apr. 24, 1998.

(51) Int. Cl.$^7$ ......................... A61K 31/52; A61K 31/34
(52) U.S. Cl. ..................... 514/261; 514/263; 514/461
(58) Field of Search ................................. 514/261, 263, 514/461

(56) References Cited

U.S. PATENT DOCUMENTS 5,446,046 A * 8/1995 Belardinelli et al. ... 514/263.24

OTHER PUBLICATIONS

Gellai et al., "CVT–124, a Novel Adenosine A1 Receptor Antagonist with Unique Diuretic Activity", J. Pharmacol. Exp. Ther. (1998), 286(3), pp. 1191–1196.*

* cited by examiner

Primary Examiner—Kevin E. Weddington
(74) Attorney, Agent, or Firm—CV Therapeutics Inc

(57) ABSTRACT

Methods and compositions for restoring diuretic and renal function.

19 Claims, 17 Drawing Sheets

METHOD AND COMPOSITION FOR RESTORING DIURETIC AND RENAL FUNCTION

CROSS-REFERENCE TO RELATED APPLICATION

This application is a continuation of U.S. application Ser. No. 09/861,873, filed May 21, 2001 that is a continuation of U.S. application Ser. No. 09/470,068, filed Dec. 22, 1999 that claims the benefit of PCT Application Ser. No. PCT/US99/08879, filed Apr. 23, 1999 that claims the benefit of U.S. Provisional Application Ser. No. 60/083,022, filed Apr. 24, 1998 and U.S. Provisional Application Ser. No. 60/083,638, filed Apr. 30, 1998; the contents of which are incorporated by reference herein in their entirety.

The present invention relates to methods of treating patients who are refractory to non-adenosine modifying diuretics by administering a combination of a non-adenosine modifying pharmaceutical composition and an adenosine A1 antagonist. The claimed methods are useful in any condition which interferes with the pre-renal signaling in such patient.

BACKGROUND OF THE INVENTION

Adenosine is an extracellular messenger generated by all cells in the body. Adenosine itself, substances that mimic the actions of adenosine, and substances that antagonize its actions have important clinical applications. Adenosine receptors are divided into subtypes designated for example as A1, A2, etc.

In most organ systems (e.g. the heart), adenosine is present exclusively during periods of metabolic stress, to mediate adaptive responses to the insult which precipitated its production and release. The kidney also releases excess adenosine in response to ischemic and toxic stimuli. In addition, however, the kidney produces adenosine constitutively to regulate glomerular filtration and electrolyte reabsorption mediated by the adenosine A1-receptor system. Adenosine receptors, when activated, can elicit either vasoconstriction (A1) or vasodilation (A2).

The A1 adenosine receptor has been found to govern the vasoconstriction response of the efferent (preglomerular) renal arteriole. Adenosine and other adenosine agonists cause a reduction in the blood flow to the kidney, and thus a reduction in the glomerular filtration rate. Thus, blocking the effects of adenosine will produce a rise in the glomerular filtration rate, and a corresponding increase in the rate of urine formation. In recent years, more selective and potent adenosine receptor antagonists have been identified, and been associated with diuretic affects.

Congestive heart failure affects millions of patients every year. Most of these patients are currently treated with diuretics to eliminate or reduce the retention of salt and water in the lungs and peripheral tissues. This pulmonary and peripheral edema causes the shortness of breath and uncomfortable ankle swelling which are common symptoms in heart failure patients. As the disease progresses, responsiveness to the currently available diuretics diminishes, and the edema becomes increasingly difficult to treat.

Problematic fluid retention is also caused by other conditions such as, for example, chronic liver diseases like cirrhoses, which in turn, produce associated abnormalities in renal function. These patients accumulate large volumes of intra-abdominal fluid, or ascites. Ascites fluid is notoriously refractory to mobilization with available diuretics. In current practice, therefore, patients are hospitalized every 1–2 months for drainage of ascites fluid through a catheter inserted directly into the abdominal cavity, i.e. paracentesis.

Diuretic resistance in conditions such as those discussed above often develops because the fraction of filtered sodium reabsorbed at the proximal tubule of the nephron increases dramatically in these patients. Consequently, diuretics acting to interrupt sodium excretion only at more distal portions of the nephron can have little or no diuretic affect.

Thus, there remains a need for compositions and methods for treating patients suffering from diuretic resistance and associated reduced renal function by regulating their body fluid and kidney function.

SUMMARY OF THE INVENTION

The presently claimed invention relates to compositions comprising a pharmaceutically effective amount of an adenosine A1 receptor antagonist and a non-adenosine modifying diuretic. The antagonist is preferably a highly potent and selective antagonist against the A1 receptor, and more preferably is BG9719, salts, isomers, esters or derivatives thereof. The diuretic can be any non-adenosine modifying diuretic, but is preferably selected from the group consisting of loop, distal or thiazide diuretics, more preferably selected from hydrochlorothiazides, furosemide, torsumide, bumetadine, thacrynic acid, piretanide, norsemide, spironolactone, tramterene and amiloriduthiazides.

The novel methods of the invention comprise the step of administering a first pharmaceutical composition comprising a therapeutically effective amount of an adenosine A antagonist in combination with a second pharmaceutical composition comprising a non-adenosine modifying diuretic. The second pharmaceutical composition can be any composition capable of inducing a diuretic effect in a patient having excess fluid. Preferably, the antagonist is a highly potent and selective antagonist against the A1 receptor, more preferably, the antagonist has a nanomolar binding affinity for the A1 receptor, and is at least 100 times more selective toward the A1 receptor than the A2a receptor. Most preferably the antagonist is BG9719, salts, isomers, esters or derivatives thereof. The diuretic can be any non-adenosine modifying diuretic, but is preferably selected from the group consisting of loop, distal or thiazide diuretics, more preferably selected from hydrochlorothiazides, furosemide, torsumide, bumetadine, thacrynic acid, piretanide, norsemide, spironolactone, tramteren and amiloriduthiazides. It is most preferable to use furosemide. In certain embodiments, the pharmaceutical compositions and methods of the invention may comprise a third component which is a diuretic which acts on a different portion of the nephron than the second pharmaceutical composition. In some circumstances, beneficial effects may result from using one or more diuretics in the second pharmaceutical composition.

The claimed methods encompass the administration of the first and second pharmaceutical compositions sequentially, or in certain instances substantially simultaneously. The preferred method comprises administering to a patient the second pharmaceutical composition comprising a non-adenosine modifying diuretic for a period of time until the patient's responsiveness to that diuretic begins to decline, or kidney function begins to decline, or both. The first pharmaceutical composition comprising the highly potent and selective antagonist can then be administered to the patient to restore diuretic responsiveness and to restore, or improve the kidney function, often as measure by a rise in GFR.

In alternative embodiments the claimed methods comprise the substantially simultaneous administration of the first and second pharmaceutical compositions. These compositions may be combined into a single tablet or formulation for ease of administration, or may comprise separate formulations so that the dosages of each may be varied to adjust to the needs of the particular patient being treated.

In the most preferred compositions and methods of the invention, the adenosine antagonist is BG9719, salts, isomers, esters or derivatives thereof, in addition to furosemide.

DETAILED DESCRIPTION

Figure 1:
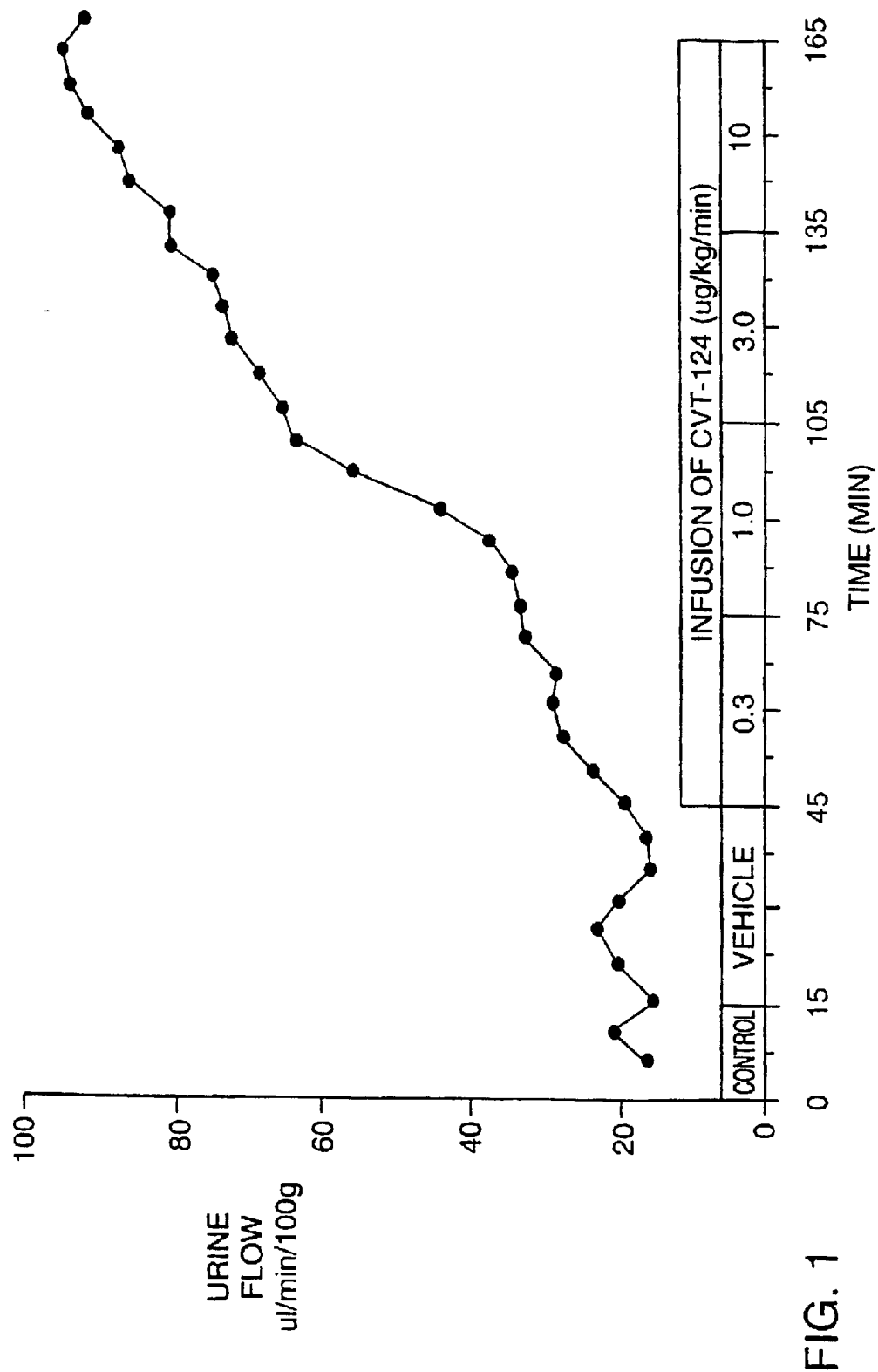
FIG. 1 is a plot of the relationship between dose of BG9719 and urine flow.

Applicants have surprisingly discovered that certain compounds which can bind to adenosine A1 receptors with high affinity and selectivity can be administered to patients suffering from congestive heart failure, or other diseases or conditions associated with edema in combination with a non-adenosine modulating diuretic (hereafter referred to as a "NAM diuretic"), without adversely affecting the glomerular filtration rate. Although adenosine A1 antagonist compounds have been known to modulate the biological activity of adenosine and have been demonstrated to be renal protective in certain renal injury models, there has been no teaching to date of the claimed methods of treating, reducing or preventing the symptoms of CHF by administering a combination of a highly selective and potent adenosine A1 antagonist and a NAM diuretic.

Various combinations of diuretics have been considered in the past, in the hope that such combinations would provide better diuresis, or increase renal function in patients in need of such treatment. Although some combinations are beneficial to patients, for example, the combination of a loop diuretic with a thiazide may increase diuresis, however it often leads to worsening kidney function. Older adenosine A1 antagonists, for example theophylline, do not have the selectivity or potency necessary to obtain the surprising advantages of the presently claimed invention. Additionally, prior combinations were not particularly useful in a clinical setting because of the toxic effects of the known adenosine inhibitors. For example, theophylline is known to have a very narrow therapeutic window since the molecule crosses the blood-brain barrier causing toxic side effects. The side effects of the less potent, and less selective adenosine antagonists would have discouraged those skilled in the art from pursuing such a combination in a clinical setting in view of these negative side effects.

Specifically, applicants have discovered that the combined administration of a highly selective and potent adenosine A1 antagonist and NAM diuretic can in effect, renew or improve the glomerular filtration rate while maintaining, increasing, or restoring diuretic responsiveness. The claimed methods are especially applicable in those edemous conditions associated with an alteration of kidney functioning, such as congestive heart failure, or ascites. Additionally, the claimed compositions and methods are equally useful in treating renal dysfunction, especially following cardiopulmonary bypass.

Antagonism of A1 receptors in the proximal and distal tubule may target relevant sites of sodium reabsorption in the nephron. Furthermore, by vasodilating the afferent arteriole, renal function may be maintained during natriuresis via inhibition of tubuloglomerular feedback.

Inhibition of proximal tubular sodium reabsorption could be beneficial in diseases such as congestive heart failure, chronic renal disease and other diseases associated with having fluid retention. Blockade of the adenosine A1 receptor represents a mechanism to induce diuresis in otherwise diuretic resistant patients, since this receptor mediates adenosine's effects on both proximal tubular reabsorption and tubular glomerular feedback. Traditional treatments for CHF, exemplified herein by furosemide, typically have numerous negative side effects, for example, loss of potassium, as well as critical reductions in glomerular filtration rates. Congestive heart failure (CHF) patients often require significant doses of furosemide or other loop diuretics to reduce the fluid load in the heart. However, the renal function of these patients often declines with continued diuresis, posing a particularly difficult clinical scenario. The reduction of renal blood flow associated with CHF results in an impaired glomerular filtration rate in these patients. In patients with CHF, increased activity of the nephron may lead to reabsorption of over 80% of the filtered sodium load in the proximal tubule. Thus, little sodium reaches the loop of Henle or distal tubule, the sites at which loop and distal acting diuretics work. Frequently CHF patients become refractory to the diuretics being administered. Often, these patients are administered an additional diuretic with a different site of action than that originally administered, in the hope of increasing urine output. However, this usually leads to an additional decrease in kidney function.

Chronic sodium retention and edema are characteristics of patients with advanced congestive heart failure, chronic renal disease and decompensated cirrhosis. Large doses of diuretics, as well as combinations of diuretics such as thiazides and loop diuretics are often required in these patients; however, their effectiveness is frequently limited. This resistance to diuretic therapy is due to decreased distal delivery of fluid as a consequence of increased proximal tubular reabsorption. Additionally, there may be a failure of the diuretic to reach its site of action. For example, the impairment in the transport of furosemide to the tubular lumen in azotemia is well documented.

The present invention is useful in treating any condition in which a patient has become refractory, or nonresponsive, to NAM diuretics, as well as conditions in which patients are experiencing a reduced response to diuretics. For example, in addition to CHF, the claimed invention may be useful for treating patients having cirrhotic ascites, or renal dysfunction following cardio-pulmonary bypass.

A number of mechanisms have been proposed as underlying the pathogenesis of ascites. Altered intra-renal hemodynamics is a hallmark feature of the pathophysiology of this disorder. There is evidence of marked afferent arteriolar vasoconstriction which may be mediated by intrarenal responses or hepatorenal reflexes. Renal dysfunction in patients with cirrhosis and fluid retention is also characterized by profound proximal tubular reabsorption of sodium, leading to a diminished daily urinary sodium output, often as low as 10 mmol. The precise mechanism for this proximal tubular reabsorption is uncertain.

The current treatment of ascites is limited predominantly to the use of aldosterone antagonists, which act by decreasing the amount of sodium reabsorbed in the distal tubule as a consequence of increased plasma renin-angiotensin (PRA) activity. Over time, the use of distal tubular diuretics (e.g. thiazides) appears to be limited by proximal tubular reabsorption, resulting in minimal distal delivery of sodium, and thus limiting the efficacy of these drugs. Loop diuretics can be effective initially, however they may lead to complications associated with a decline in renal function, occasionally leading to hepatorenal syndrome. Over time, the use of loop diuretics is again limited by proximal tubular reabsorption of sodium and failure of delivery to the loop of Henle.

Patients who develop resistance to diuretic treatment presently may require paracentesis, and/or liver transplantation. Thus, the claimed compositions which antagonize the adenosine A1 receptors in both the proximal and distal tubule may target relevant sites of sodium reabsorption, and may restore diuretic responsiveness to refractory or resistant patients when given in combination with a NAM diuretic.

The claimed methods in certain embodiments encompass the administration to patients refractory to NAM diuretics, such as those suffering from ascites or CHF, of an adenosine A1 antagonist while maintaining the diuretic therapy. Surprisingly, this results in not only a nearly complete renewal of the diuretic function of the NAM diuretic component, but also results in a renewal or increase in the glomerular filtration rate, without negative side effects. Therefore, the excess fluid can be removed more quickly and effectively, without the associated side effects of administering a NAM diuretic alone. Additionally, the combination of an adenosine A1 antagonist and a NAM diuretic when administered to an edemic patient results in a synergistic amount of weight loss. (See FIG. 14)

Any highly potent, highly selective adenosine A1 antagonist may be used in the present invention. Many of these antagonists have been previously shown to have diuretic effects. However, there has to date been no teaching or suggestion of a combination of NAM diuretics with a highly potent and selective adenosine A1 antagonist to restore diuretic responsiveness and improve glomerular filtration rate. Nor has there been any teaching or suggestion of the synergistic weight loss resulting from the claimed methods and compositions.

The preferred adenosine A1 antagonists of the invention may include, but are not limited to, 1,3-dipropyl-8-[5,6-exo-epoxy)-2(S) norbornyl] xanthine shown in Formula 1, and referred to hereinafter as BG9719. See, for example, U.S. Pat. Nos. 5,446,046; 5,631,260; and 5,668,139, specifically incorporated by reference herein, which describe the preferred adenosine antagonists of the claimed invention as well as methods of making them.

Formula 1

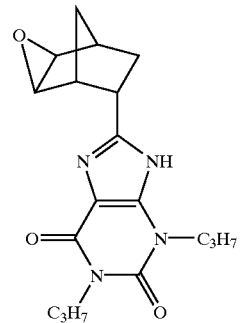

The preferred adenosine A1 antagonists of the invention also encompass isomers of BG9719, salts, esters, or derivatives.

BG9719 possesses unique diuretic properties resulting in potassium-sparing diuretic activity as well as enhancing the natriuretic and diuretic activity of a loop diuretic without further increasing potassium excretion. Additionally, as a hydrophilic compound, it does not suffer from the negative effects of crossing the blood brain barrier, as do other, lipophilic adenosine A1 antagonists such as theophylline. Thus, BG9719 in combination with a NAM diuretic represents a novel therapy for patients with fluid retaining disorders. BG9719 is a highly selective adenosine A1-receptor antagonist that causes natriuresis by reducing adenosine A1-mediated sodium reabsorption in both the proximal and distal tubules of the nephron with only minimal potassium loss. In addition, antagonism of adenosine A1-mediated constriction of the afferent arteriole by BG9719 interrupts tubuloglomerular feedback Thus it interferes with the kidney's ability to downregulate the GFR in response to a high salt load in the distal nephron without causing negative side effects. The resulting maintenance of GFR further contributes to the natriuretic effect of BG9719 and prevents the decline in renal function often associated with the treatment of volume overload in congestive heart failure.

In addition to restoring or preserving the diuretic response to its more proximal effects, inhibition of Na+/K+ exchange in the distal tubule by adenosine A1 antagonists prevents potassium wasting associated with enhanced delivery of sodium to the distal tubule. Loop diuretics, for example, are often associated with substantial potassium loss, as Na+/K+ exchange in the distal tubule increases to compensate for the inhibition of chloride and sodium reabsorption caused by these drugs in the loop of Henle. By inhibiting distal Na+ reabsorption with consequent inhibition of K+ excretion, use of adenosine A1 antagonists in combination with traditional diuretics offers the potency of loop diuretics while minimizing potassium loss.

Any diuretics are useful in the present invention. For example, thiazide diuretics are widely administered and include hydrochlorothiazides, benthiazide, chlorothiazide, and the like, acetazolamide and its analogs, ethacrynic acid. Other diuretics include loop-acting diuretics such as furosemide, bumetanide, amiloride, thacrynic acid, piretanide and norsemide. potassium-sparing diuretics such as spironolactone, triamterene and amiloride.

The claimed methods are not intended to be temporally limited. For example, in some instances, a patient may be first treated with a traditional diuretic for a period of days, hours or weeks. When the patient is no longer responding sufficiently to said diuretic, the patient may then be administered the adenosine A1 antagonist of the invention. This combined administration will then restore the responsiveness to the originally administered diuretic, as well as restore or increase the patient's GFR.

In other embodiments, both the adenosine antagonist and the diuretic are administered substantially concomitantly, in either separate dosage forms, or by administration of a single pharmaceutical composition comprising both active ingredients. The preferred timing and method of administration will depend upon the severity of the patient's condition, as well as other factors known to those of skill in the art.

In acute settings, it may be preferable to administer the claimed compositions intravenously, although, other routes of administration are equally acceptable. In some embodiments, it may be useful incorporate into the claimed pharmaceutical compositions additional therapeutic compositions as desired.

The compounds of the invention can be formulated with pharmaceutically effective carriers into compositions that can be administered to a patient. The pharmaceutical compositions of this invention may be orally administered in any orally acceptable dosage form including, but not limited to, capsules, tablets, enteric coated tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

Standard procedures for administration of adenosine antagonists such as theophylline and aminophylline, and diuretics such as furosemide or spironolactone at effective dosages are well established and are well known to those skilled in the art.

Preferred are methods of administration which allow rapid access to the tissue or organ being treated, such as intravenous injections.

Pharmaceutical compositions containing the active ingredient may be in any form suitable for the intended method of administration. When used for oral used, for example, tablets, lozenges, aqueous or oral compositions, powders, syrups or elixirs may be prepared. Compositions intended for oral use may be prepared according to any method known to the art for the manufacture of pharmaceutical compositions, and such compositions may include one or more agents including sweetening agents, flavoring agents, coloring agents and preserving agents, in order to provide a palatable preparation. Tablets containing the active ingredient in admixture with non-toxic pharmaceutically acceptable excipients are also acceptable. These excipients may be, for example, inert diluents, such as calcium or sodium carbonate, lactose, calcium or sodium phosphate, granulating and disintegrating agents, binding agents and lubricating agents. Tablets may be uncoated or may be coated by known techniques.

Additionally, the pharmaceutical compositions may be formulated as solutions or suspensions, according to methods known in the art.

EXAMPLE 1

In 12 patients on ACE inhibitors, ages 59.3+/−10.5 years with NYHA Class II or III CHF, the effects of BG9719 on renal function were compared to placebo and furosemide. Patients received a single intravenous dose of BG9719 (1.0 mg/kg) or placebo in a randomized, double-blind, crossover fashion on each of 2 dosing days, followed by an open-label dose of I.V. furosemide (equivalent to the patient's usual daily oral dose) on a third dosing day. GFR was determined using plasma radionuclide measurements. Compared to placebo, GFR did not change on BG9719. In contrast, GFR fell in patients receiving furosemide. Sodium and urine excretion increased with either BG9719 or furosemide, although the treatments were not equinatriuretic. There was no effect on renal plasma flow.

| Effects of BG9719 and Furosemide versus Placebo, 0–2 hours (mean ± SD[N]) | | | |
|---|---|---|---|
| GFR (mL/min/1.73 m$^2$) | 81.5 ± 23.5 (12) | 79.6 ± 23.8 (11) | 63.4 ±) 18.0 (11) |
| RPF (mL/min/1.73 m$^2$) | 296 ± 118 (12) | 334 ± 148 (12) | 370 ± 221 (12) |
| NA + excretion (mEq) | 8.57 ± 7.47 (12) | 36.7 ± 26.0*** (12) | 103 ± 77.9* (6) |
| Urine volume (mL) | 156 ± 107 (12) | 501 ± 293* (12) | 1081 ± 529* (12) | p values are intrapatient drug-placebo: *$^2$0.05, $^2$0.01, *$^2$0.001

EXAMPLE 2

Methods

Animals

All procedures were approved by the Institutional Animal Care and Use Committee and were in accordance with NIH Guidelines for the care and use of animals.

Male Sprague-Dawley rats were obtained from Charles River Labs (Wilmington, Del.). They were housed in a light-controlled room with a 12 h light/dark cycle and were allowed ad libitum access to food and water.

Surgical Preparation

Catheters were implanted in the abdominal aorta and vena cava via the left femoral artery and vein under a mixture of ketamine hydrochloride (50 mg/kg) and acepromazine (0.2 mg/kg, i.m.) anesthesia. An additional medical grade Tygon tubing was placed in the he stomach at the left extremity of the greater curvature. A silastic-covered stainless steel cannula was implanted in the bladder. Details of surgery, pre and post-surgical care and the experimental set-ups have been described in detail previously (87). Experiments were conducted 4–5 days following surgery, by which time the rats had fully recovered and were gaining weight. During the recovery, the rats were housed individually and were accustomed to a plastic retainer (model ECU, Braintree Scientific, Inc., Braintree, Mass.).

Experimental Procedures

Between 8:00–9:00 AM, rats were weighed and placed in the restrainer. The arterial line was connected to a Gilson polygraph via a Gould pressure transducer for the recording of blood pressure (MAP) and heart rate (HR); the venous line to infusion pumps for the infusion of vehicle and test agents; and the stomach tube to a 10 or 20 cc syringe to allow for the replacement of excess urinary loss. The bladder cannula was extended with a short length of PE tubing to permit collection of urine into preweighed tubes.

To replace normal fluid and electrolytes loss, heparinized (50 U/ml) ringer's solution was infused throughout the experiment via the arterial line and 5% dextrose during the equilibration and control period via the venous line, each at 10 µl/min. When excess fluid loss reached 2 ml, it was replaced via the gastric tube with room temperature Ringer's solution. A period of 45–60 min was allowed for equilibration in all studies, at the end of which a 0.5 ml blood sample was taken for measurement of hematocrit, plasma electrolytes and creatinine. This was followed by the various experimental procedures described below.

Group 1. Sustained I.V. infusion of diuretic agents. Urine was collected in 5 min periods throughout the experimental period. After equilibration, 3 collections were made to establish baseline. thirty min urine collections were made before and during infusion of test agent. The infusion rates for each diuretic agent were determined in preliminary experiments, and were (µg/kg/min): 0.3, 1, 3 and 10 for BG9719 (n=5): 10, 30, 100, and 300 for FUR (n=5), and 3, 10, 30 and 100 for HCTZ (n=7). At the end of experiments, the rats were weighed again and returned to their home cages.

Group 2. Sustained i.v. infusion of combinations diuretics. Following equilibration, control collections and infusion of appropriate vehicles, a combination of FUR and BG9719 (10 and 1 µg/kg/min, respectively), or FUR and HCTZ (10 and 30 ug/kg/min, respectively) was infused for 30 min at a rate of 10 µl/min. After the termination of infusion, urine flow was allowed to return to baseline, approximately 15–20 min. The rats were then weighed and returned to their home cages.

Group 3. Renal clearance studies BG9719 and furosemide. Insulin (10%) and PAH (2%) were infused i.v. at 20 µl/min from the start. IN order to establish baseline values, two 20 min urine collections were performed following equilibration. One blood sample (500 µl) was taken in the middle of the second collection. Subsequently, vehicle, BG9719 (1 µg/kg/min) or FUR (10 µg/kg/min) was infused for 90 min, during which time three 30 min urine collections were performed, and a further blood sample taken between the second and third period.

Analytical and Data Analysis

Urinary and plasma concentrations of insulin and PAH were determined by spectrophotometry, electrolyte concentrations were measured using the Synchron ASB Clinical System (Beckman Instr. Inc., Brea, Calif.) and osmolality by an automatic osmometer (Model 2430, Precision Systems, Inc., Natick, Mass.). Renal clearance values were calculated using standard clearance formulae and expressed per 100 g body weight.

All values represent maximal changes, expressed as absolute values, and are reported throughout as group means+−SEM. Data from the does-response studies (groups 1–5) were analyzed using an analysis of variance for repeated measures, post-hoc comparisons were made with the Schette f-test. Analysis of variance (ANOVA) was used to analyze differences between the effects of various diuretics and their combinations (group 6) and the renal clearance data (group 7). A value of $P<0.05$ was considered statistically significant.

Drugs and Solutions

BG9719, furosemide and hydrochlorothiazide (Sigma Chemical Co., St. Louis, Mo.) were prepared daily in a mixture containing 20& ethanol, 30% PEG 200 and 50% sterile water.

Results

Careful replacement of fluid and electrolyte loss ensured the maintenance of fluid and electrolyte homeostasis, with the exception of a small decrease in plasma potassium levels in one group of animals (Table 1). Fluid replacement prevented severe volume contraction, thus permitting evaluation of does-response effects and duration of action of diuretic agents. Mean basal blood pressure (112±4 mmHg) and heart rate (368±14 beats/min) were not different between groups, and there was no change in either parameter during any of the studies.

Dose response studies. Infusion of BG9719 resulted in a does-dependent increase in urine flow as demonstrated in a representative experiment (FIG. 1). Infusion in vehicle had no significant effect on urine flow and sodium exectretion (FIG. 1). The total urine output for the animal tested in FIG.

Figure 2A:
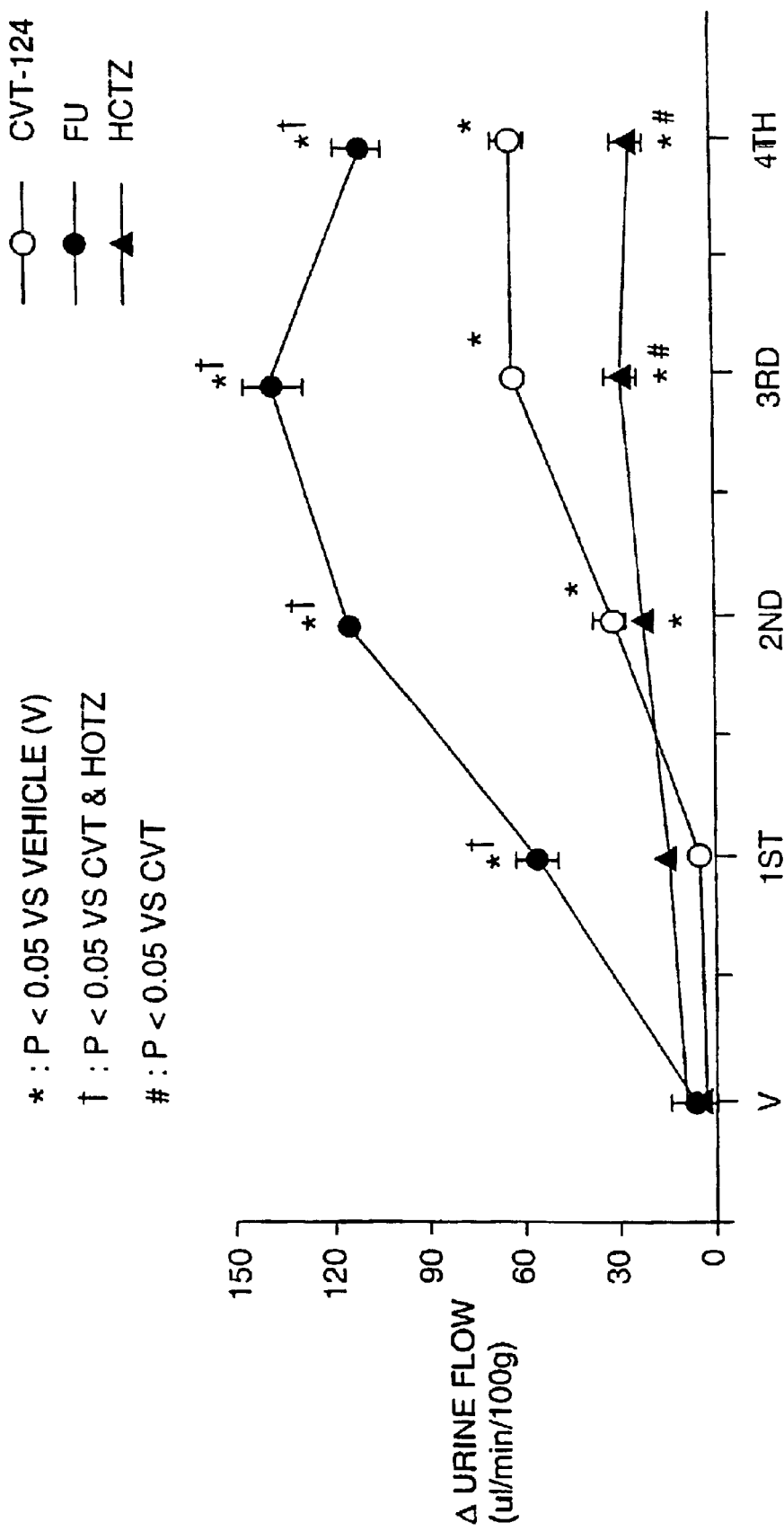
FIGS. 2A, 2B and 2C are plots comparing urine flow, sodium excretion and potassium excretion respectively based upon-number of doses of BG9719, Furosemide, and HCTZ.
Figure 2B:
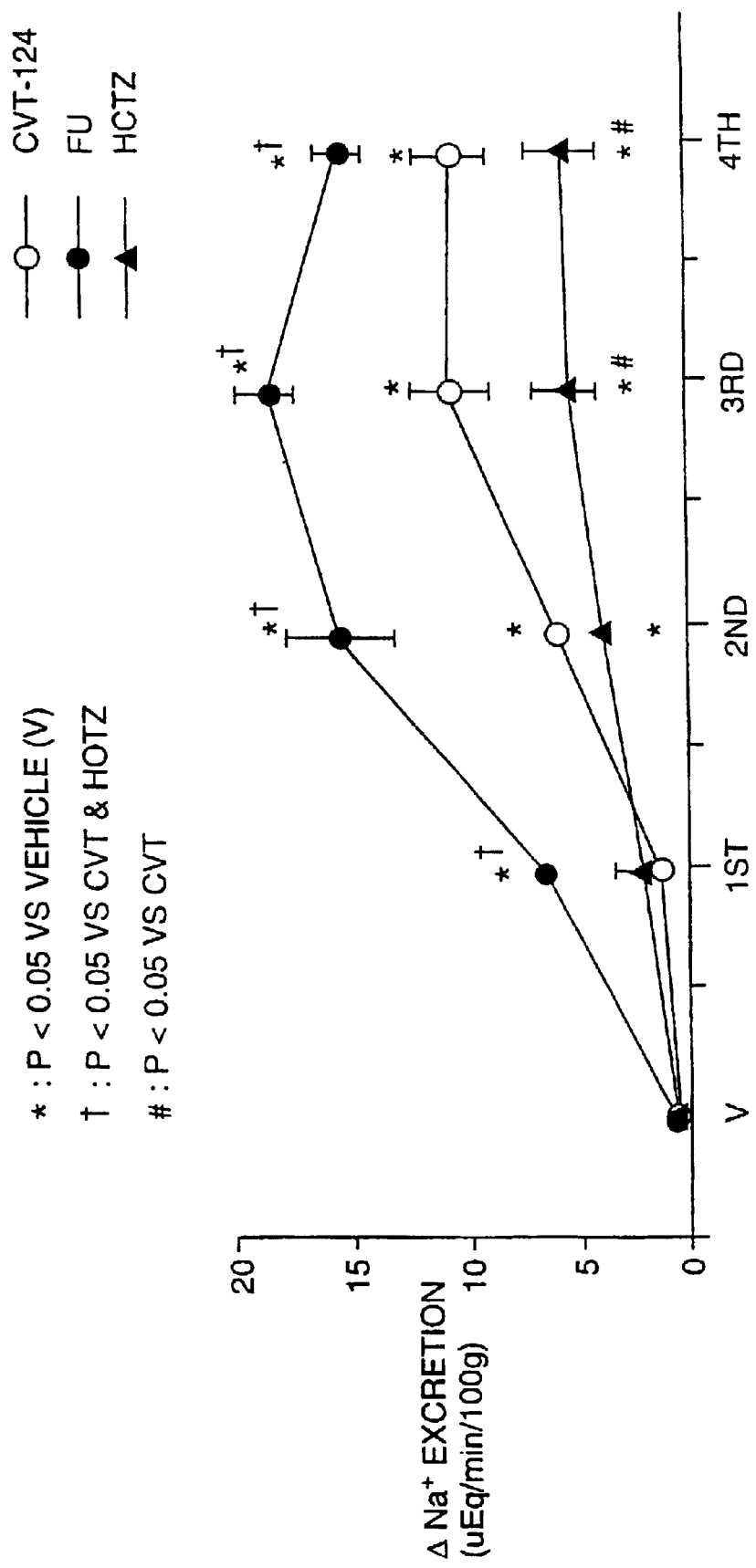
Figure 2C:
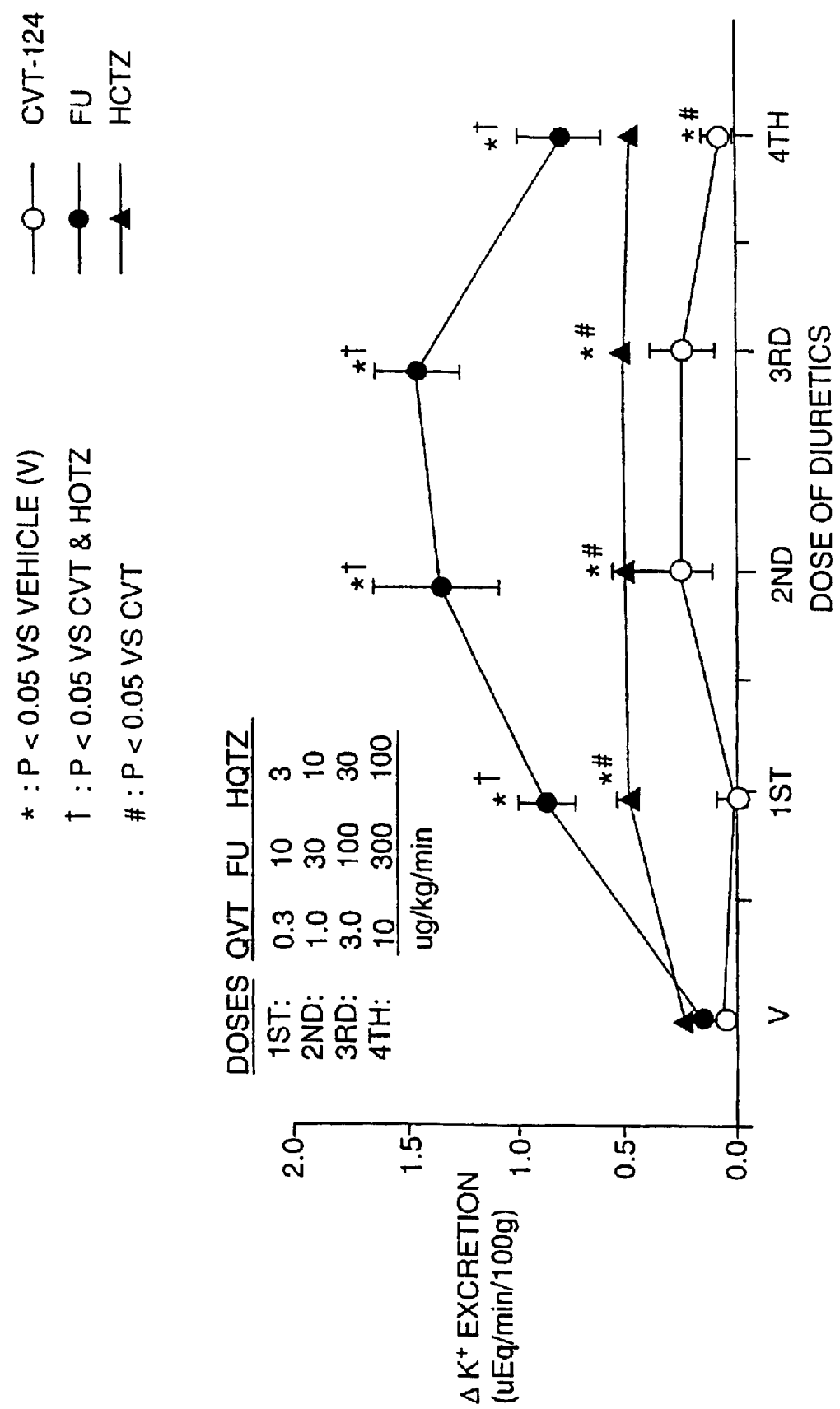

1 was 23.8 ml. The maximum diuretic effects of BG9719, FUR and HCTZ were reached with doses of 3, 100 and 20 μg/kg/min, respectively (FIG. 2). Furosemide was twice as a potent diuretic as BG9719 whereas HCTZ had only minor effects (FIG. 2 & Table 2). Potassium excretion was significantly increased with FUR and HCTZ, but not with BG9719. Excretion of urea slightly increased with the lowest doess (data not shown), but returned to baseline during the infusion of higher doses (Table 2). In these, as well as the following studies (groups 2&3), the increase in urine flow was solely due to the increase in the excretion of solutes (Cosm). Clearance of free water, $CH_2O$ was not altered (Table 2).

Figure 3A:
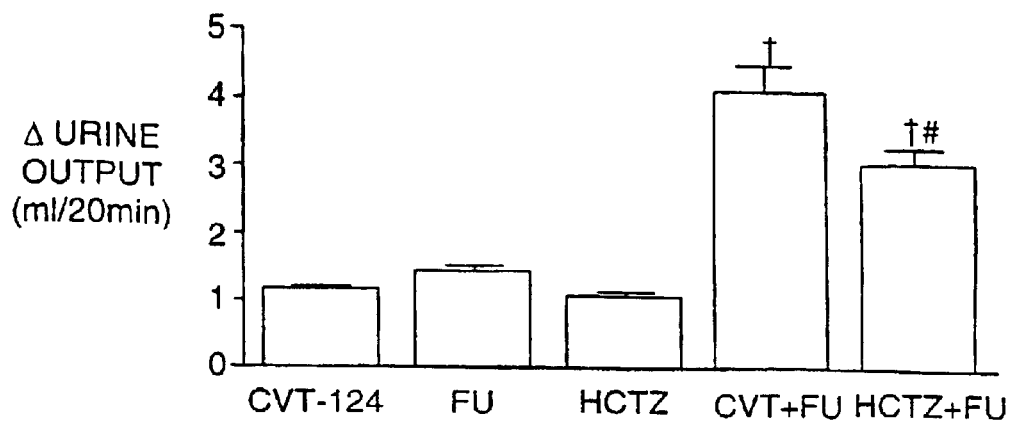
FIGS. 3A, 3B and 3C are bar plots of the effect of doses of BG9719, Furosemide, and HCTZ, and combinations thereof on change in urine output, change in urine sodium content, and change in urine potassium content.
Figure 3B:
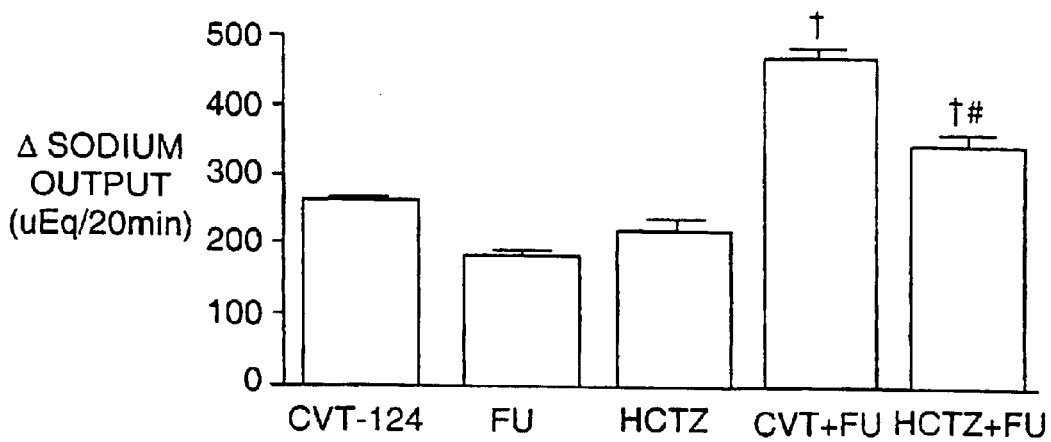
Figure 3C:
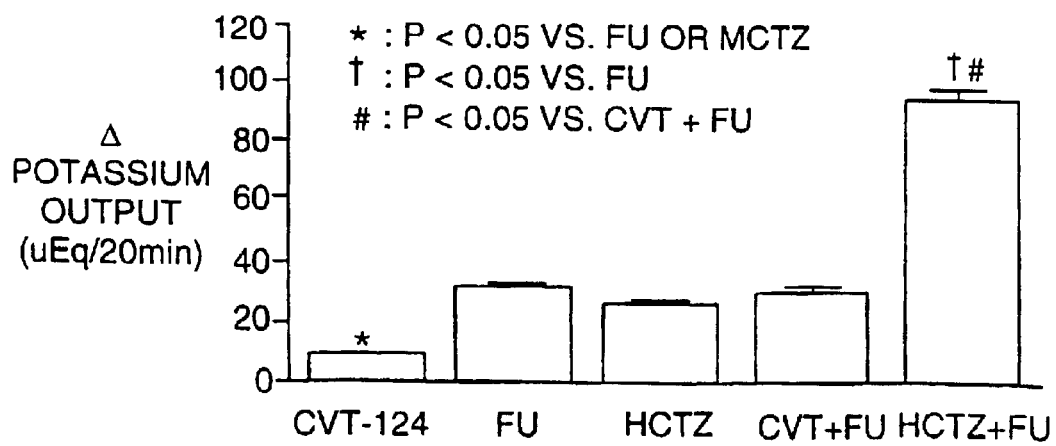

Combination studies. Equidiuretic doses of BG9719, FUR and HCTZ were 1, 10 and 30 μg/kg/min, respectively. Combinations of FUR+BG9719, or FUR+HCTZ both elicited an additive diuretic effect as illustrated by the 30 min urinary output (FIG. 3). BG9719 and HCTZ, however, affected FUR's action on electrolyte excretion differently. BG9719 significantly potentiated the natriuretic effect of FUR in an additive manner without further increasing its kaliuretic effect. In contrast, HCTZ (hydrochlorothiazide) significantly increased the kaliuretic action of furosemide, and only moderately increased its natriuretic effect (FIG. 3).

Figure 4A:
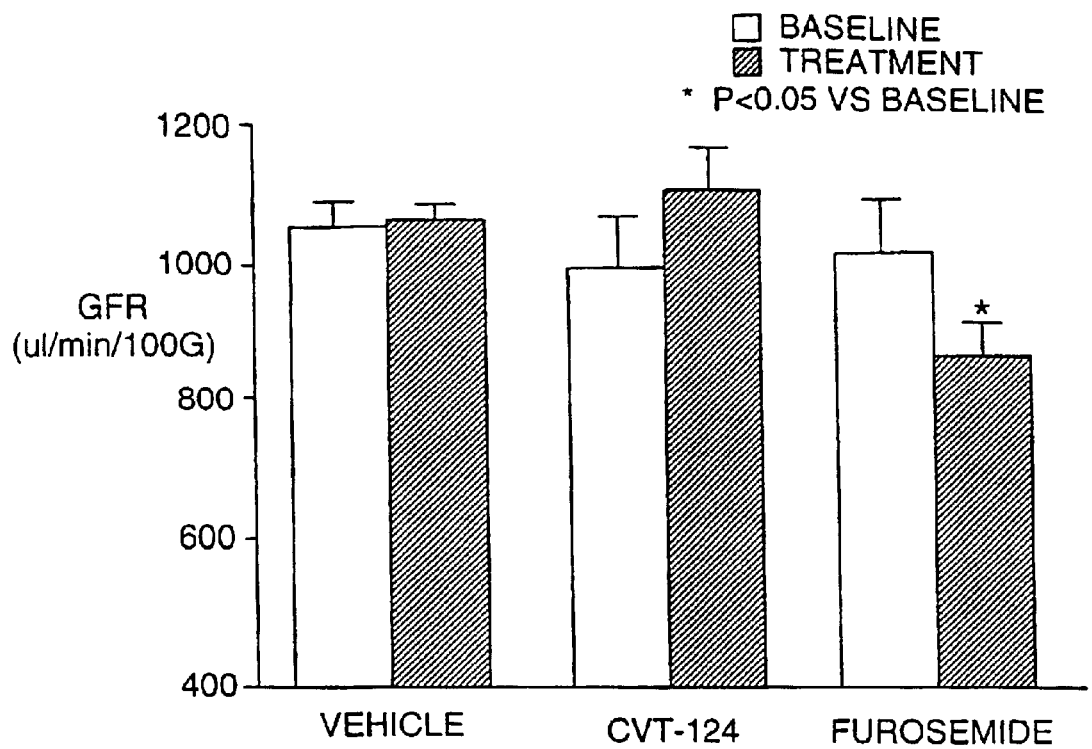
FIGS. 4A and 4B are plots of the effect of BG9719; Furosemide, and the inert vehicle on GFR and RBF.
Figure 4B:
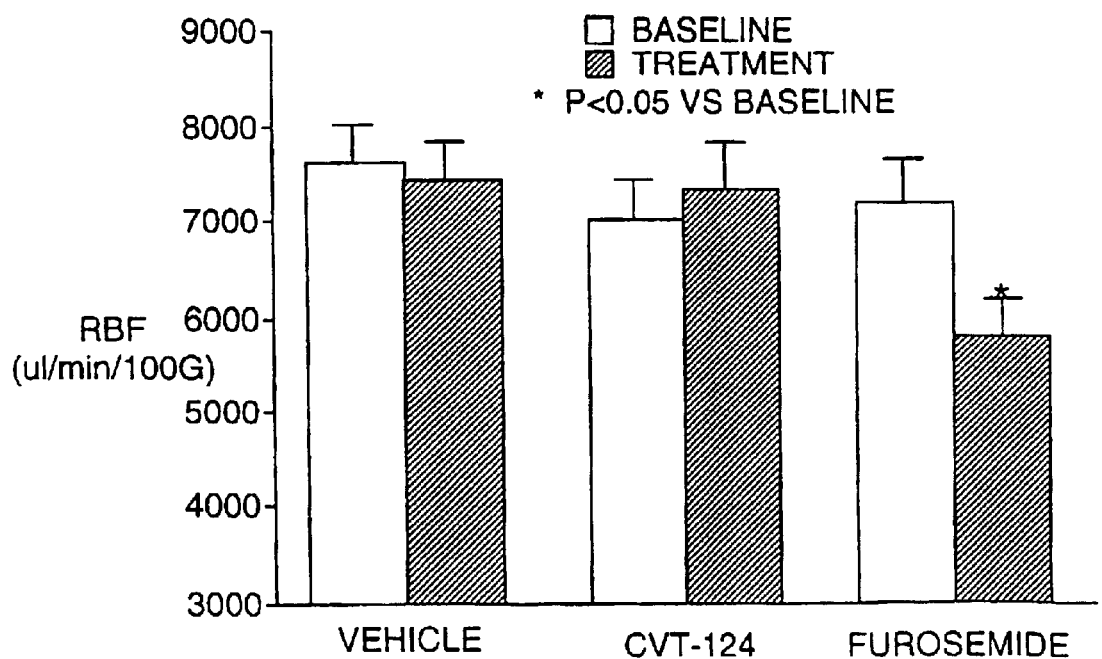
Figure 5A:
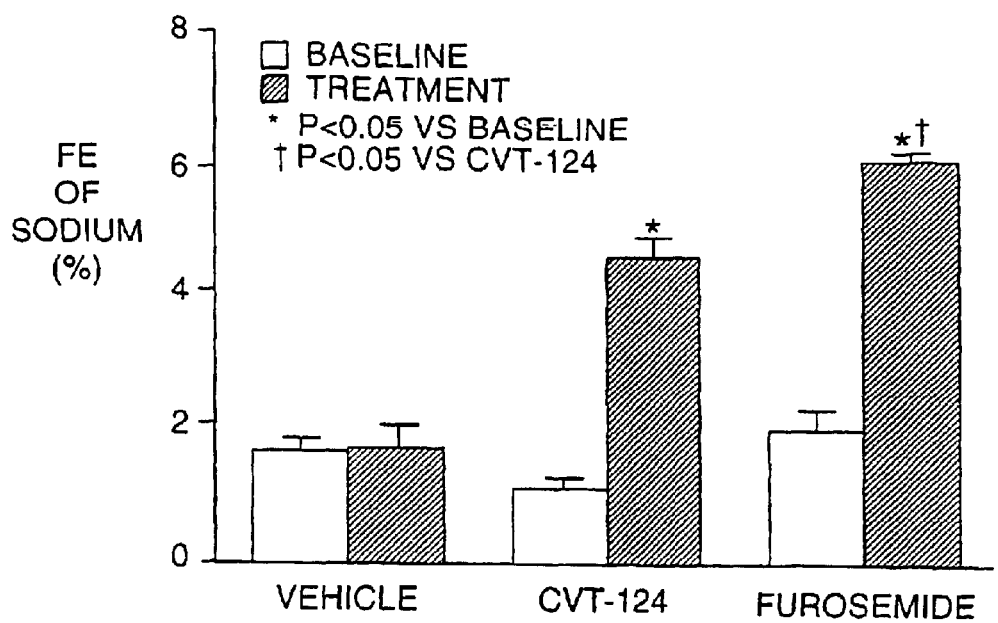
FIGS. 5A and 5B are plots of the fractional excretion of sodium and potassium after administration of the inert vehicle, BG9719 or Furosemide.
Figure 5B:
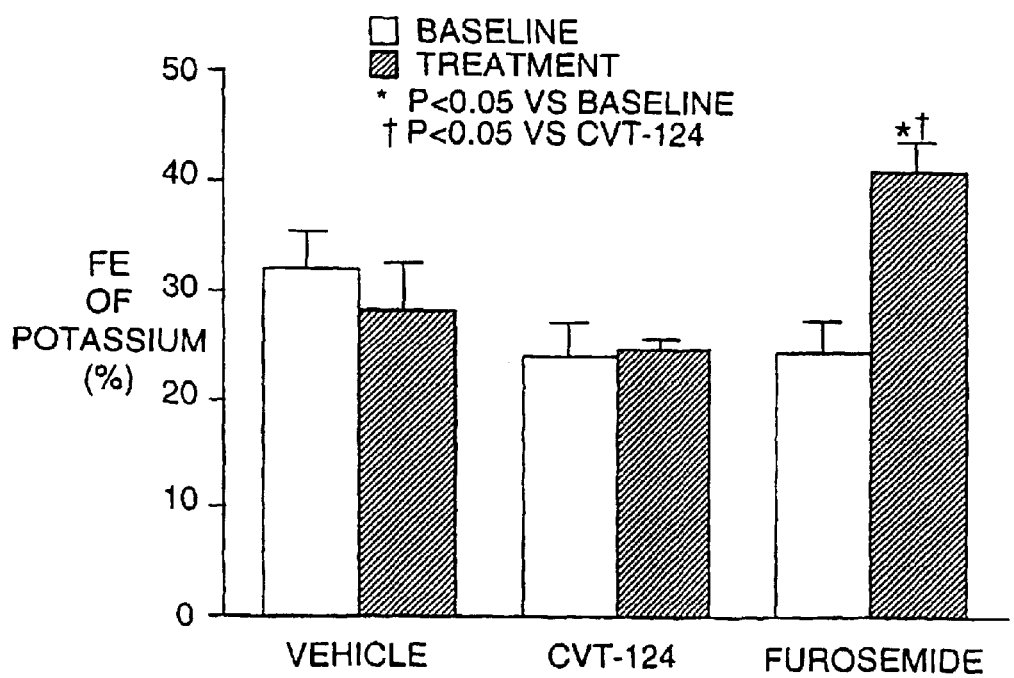

Effect of BG9719 and furosemide on renal hemodynamics. Sustained infusions of vehicle had no effect on GFR and RBF, or on the fractional excretion of electrolytes (FIGS. 4 & 5). BG9719 moderately (13%) increased GFR, however, the change was not statistically significant. In contrast, FUR infusion significantly lowered GFR and RBF (FIG. 4). Both compounds increased the absolute and fractional excretions of sodium, but only FUR increased the fractional excretion of potassium (FIG. 5).

The selective adenosine A1 receptor antagonist, BG9719, possesses remarakable diuretic activity. Administered alone, BG9719 increased urine flow and sodium excretion without affecting either potassium excretion or renal hemodynamics. Its maximal effects were greater than that observed with HCTZ which was associated with a significant kaliuresis. The effect of BG9719 was not as great as furosemide. However, furosemide administration was associated with large increases in potassium excretion. This was in contrast to HCTZ which, when given in combination with FUR, resulted in a 3-fold increase in potassium excretion. This ability of BG9719 to enhance the effect of FUR without further increasing potassium excretion is an important observation since there is an abundance of data demonstrating the combined use of loop and thiazide diuretics results in hypokalemia and potentially serious side effects.

These data suggest BG9719 when given alone or in combination with a loop diuretic will provide an important therapeutic tool in patients with congestive hear failure, chronic renal disease or cirrhosis. In addition, its unique mechanism of action suggests that BG9719 will be effective in otherwise diuretic-resistant patients. In addition to stimulating sodium reabsorption in the proximal tubule, adenosine activates the tubular glomerular feedback mechanism and inhibits chloride transport in the collecting duct. This, activation of the tubular glomerular feedback mechanism as well as distal sodium chloride reabsorption would not negate the proximal tubular effects of BG9719. Micropuncture studies demonstrating increased flow rates in both the proximal and distal tubules following administration of BG9719 support this. In addition, adenosine-induced inhibition of Na/K exchange in the distal tubule could provide the mechanism for the observed potassium-sparing activity of BG9719.

The diuretic and natriuretic effects of adenosine A1 receptor blockade have been reported previously. Indeed, adenosine antagonists have been shown to increase sodium excretion in animals as well as hyptertensive patients and normal volunteers. The successful development of adenosine receptor antagonists, however, has been complicated by receptor selectivity. Thus, many adenosine A1 receptor antagonists also possess some degree of A2 receptor antagonist activity. Any such activity would lead to cardiac liabilities since antagonism of cardiac A2 receptors would oppose adenosine-mediated coronary vasodilation. BG9719 is one of the most potent and selective adenosine A1 receptor antagonists yet identified. Its $IC_{50}s$ for the A1 and A2 receptors are 1.15 and 9000 nM, respectively, representing a 7800-fold selectively for the A1 receptor. The selectively profile of BG9719 is superior to that of some of the other adenosine A1 receptor antagonists, such as KW 3902 and CPX, which demonstrate A1 vs. A2 selectivity of 150 and 60 fold, respectively.

EXAMPLE 3

Figure 6:
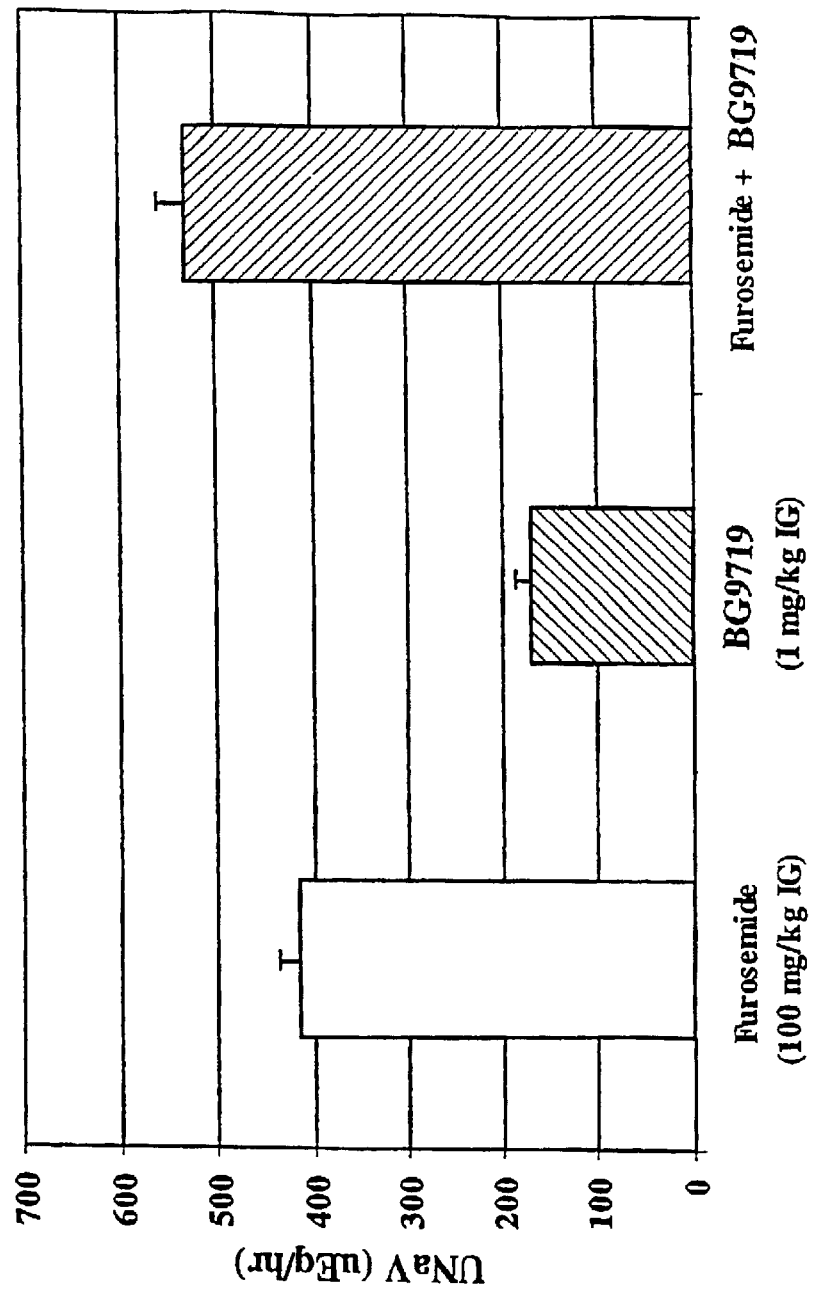
FIG. 6: Naive rats (n=6 per group) were dosed with either furosemide (100 mg/kg—a near maximal dose), BG9719 (1 mg/kg—a maximal dose) or the combination of furosemide and BG9719. Urines were collected for 4 hours post dosing and the natriuretic response was determined. The data are expressed as uEq/hr. As shown, furosemide increased sodium excretion to ~400 uEq/hr while BG9719 causes a lesser effect—~175 uEq/hr. Administration of both compounds yielded an additive effect, wherein sodium excretion increased to ~525 uEq/hr.

Twenty four male Sprague-Dawley rats were placed in metabolic cages to collect urines in order to assess the natriuretic response to orally administered compounds. Eight rats received furosemide at 100 mg/kg by gavage, eight rats received BG9719 at 1 mg/kg by gavage and eight rats received both compounds in a combination dose. Urines were collected for 4 hours after dosing. Urine volume was determined gravimetrically and urinary sodium concentration was determined by flame photometry. Sodium excretion (UNaV; uEq/hr) was calculated from these values. As shown in FIG. 6, furosemide (100 mg/kg IG) elicits a robust natriuresis while the response to BG9719 is lower. When dosed together, the results indicate an additive natriuretic response.

EXAMPLE 4

Sixteen male Sprague-Dawley rats received once daily doses of either furosemide or BG9719 for seven days. One half of the rats received furosemide by gavage at 100 mg/kg. The other half received BG9719 by gavage at 1 mg/kg. Body weight was determined prior to dosing each day.

Figure 7:
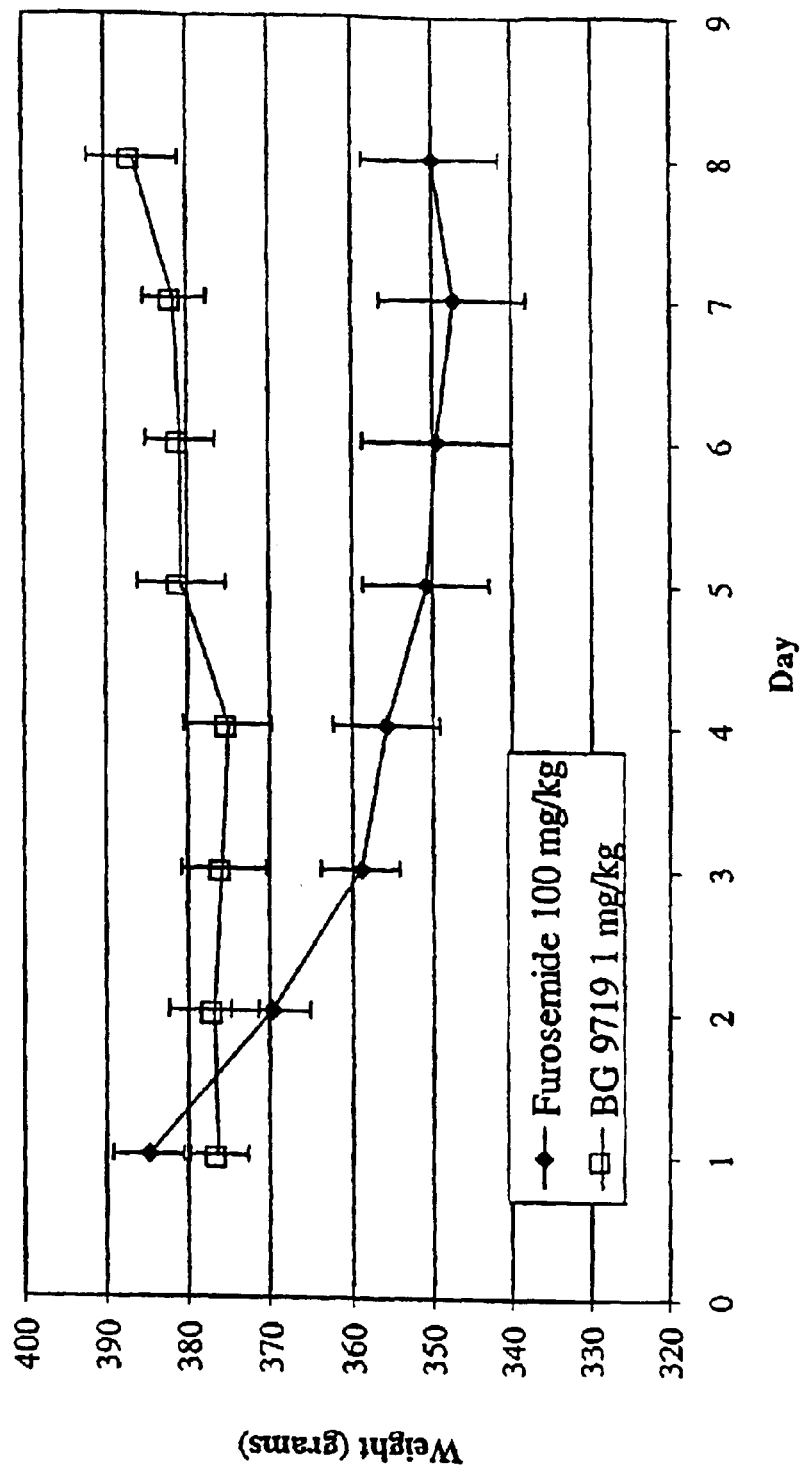
FIG. 7: Rats (n=6 per group) were dosed once-per-day with either furosemide (100 mg/kg) or BG9719 (1 mg/kg) for 8 days. The rats were weighed prior to each day's dosing and the results are plotted on this graph.

As shown in FIG. 7, furosemide induces a loss in body weight after the first and second dose but this effect was not sustained with subsequent dosing. Therefore, once the rats develop 'tolerance' to the loop diuretic, this dosing strategy with furosemide does not induce a loss in body weight. Dosing with BG9719 did not induce a loss in body weight.

EXAMPLE 5

Figure 8:
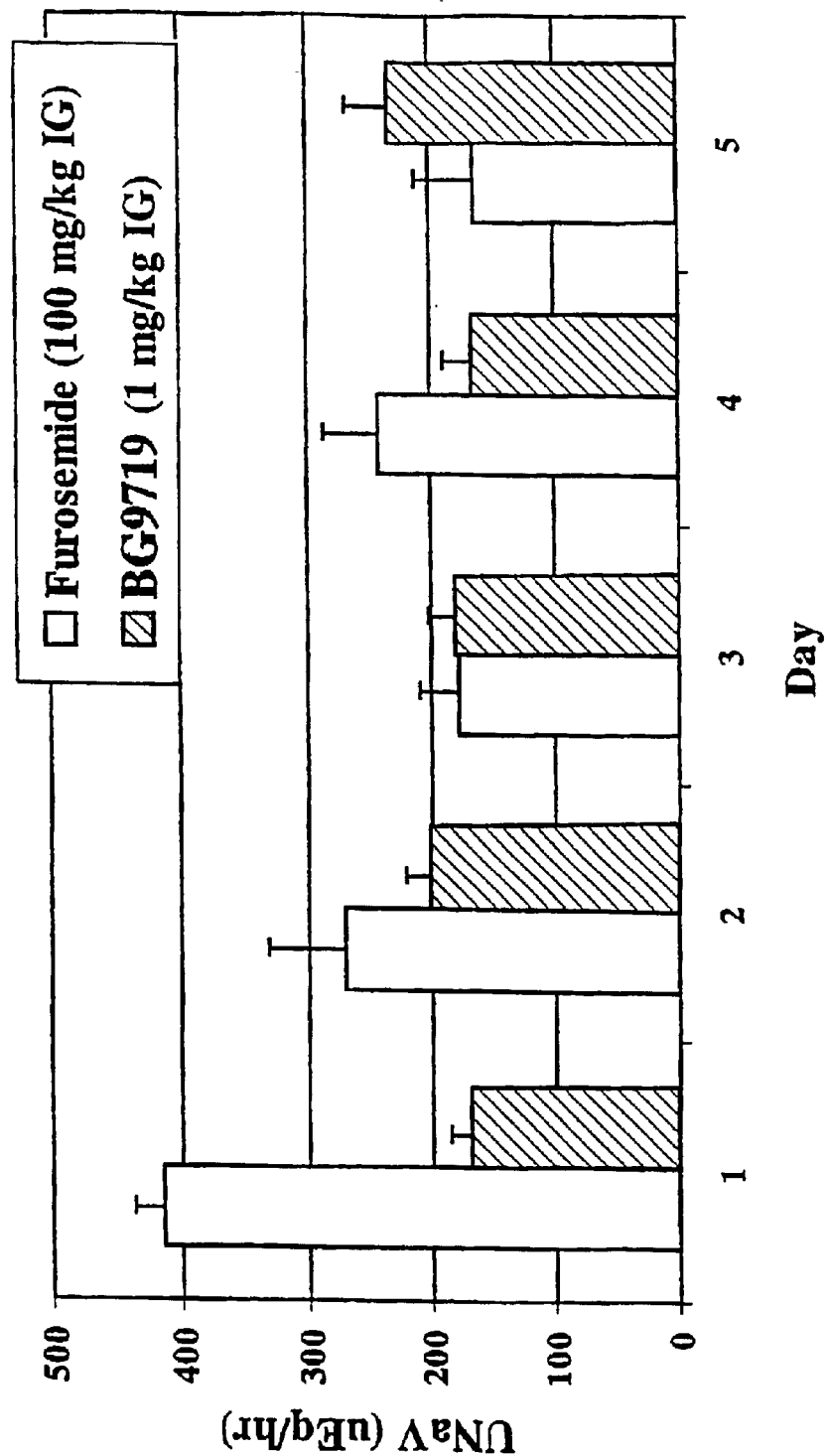
FIG. 8: In the same rats from FIG. 7, we collected urine for 4 hours after dosing. The sodium excretion data from the first 5 days are shown on this graph.

The rats shown in Example 4 were placed in metabolic cages on Days 1 through 5 of dosing and urine was collected for 4 hours after dosing. Urine volume was determined gravimetrically and urinary sodium concentration was determined by flame photometry. Sodium excretion (UNaV; uEq/hr) was calculated from these values. As shown in FIG. 8, the natriuretic response to furosemide diminishes on repeated dosing such that the response on Days 3 to 5 are not different than the response achieved with dosing with BG9719. The natriuretic response to BG9719 is maintained across multiple dosing days.

EXAMPLE 6

The rats in Examples 4 and 5 which received furosemide once per day were dosed with a combination of furosemide (100 mg/kg by gavage) and BG9719 (1 mg/kg by gavage) on Day 8 (Furo+BG9719). They were placed in metabolic cages and urines were collected for four hours after dosing. Urine volume was determined gravimetrically and urinary sodium concentration was determined by flame photometry. Sodium excretion (UNaV; uEq/hr) was calculated from these values.

Figure 9:
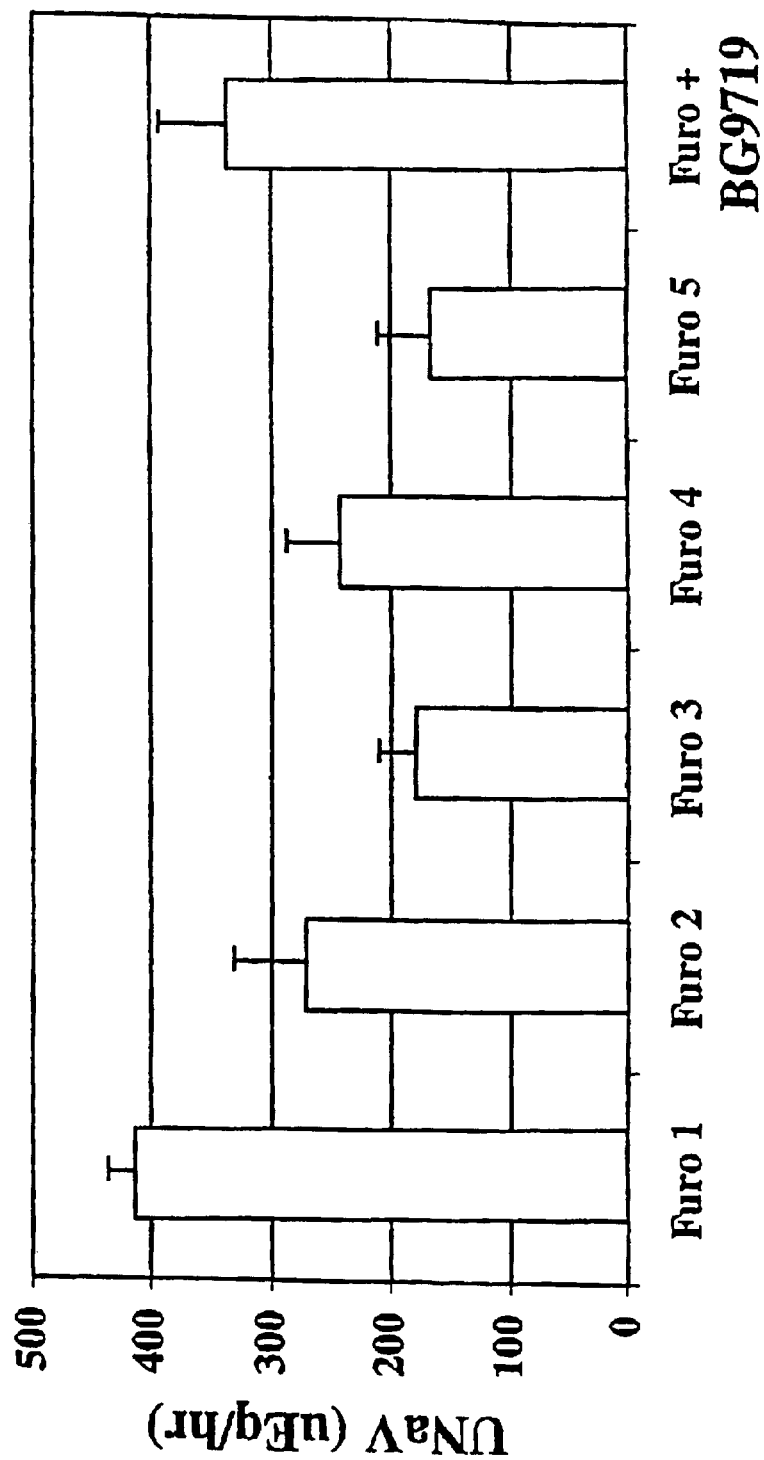
FIG. 9: This is a re-plot of the furosemide data on FIG. 8, with the addition of the last treatment. After 8 days of furosemide treatment, the rats received a combination of furosemide and BG9719. The natriuretic response to the combination appears to demonstrate an additive effect of the two drugs.

As shown in FIG. 9, combination dosing with furosemide and BG9719, after the induction of furosemide 'tolerance', results in an increased natriuresis over that observed with furosemide alone on Day 5.

EXAMPLE 7

Figure 11:
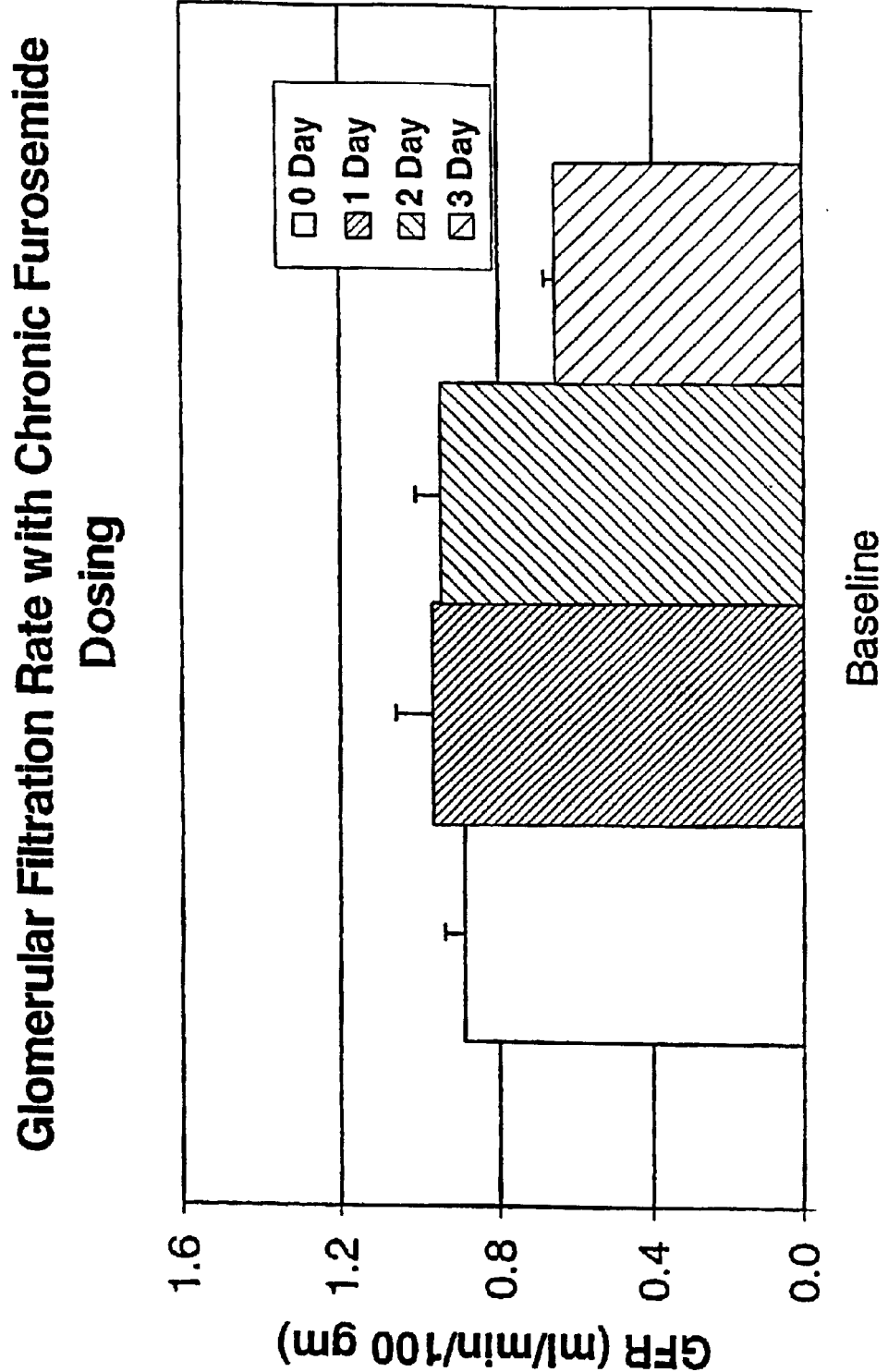
FIG. 11: Rats were dosed with 100 mg/kg furosemide orally for either 1, 2, or 3 days. Twenty four hours after their last dose, they were anesthetized and instrumented to measure renal function and hemodynamics. Their basal glomerular filtration rate are shown in this slide. As shown, GFR is fairly normal (1–1.2 ml/ml/100 is normal) after 1 day of furosemide dosing. GFR is decreased after two days of dosing and further decreased after 3 days of dosing. After 3 days, GFR is reduced to ~50–60% of normal.

Male Sprague-Dawley rats were dosed by gavage with furosemide at 100 mg/kg for either 1, 2, or 3 days. An additional group (0 Days) was not dosed with furosemide. Twenty-four hours after the last dose was administered, the rats were anesthetized and instrumented to measure renal function. Insulin was infused intravenously and concentrations of insulin in plasma and urine were determined by a biochemical assay. The urinary clearance of insulin was used as a measure of glomerular filtration rate. Urine was collected via an implanted bladder catheter. Urine volumes were determined gravimetrically and urinary sodium concentration was measured by flame photometry. Sodium excretion (UNaV; uEq/hr) was calculated from these values. Following a baseline collection period, each rat received a single intravenous bolus dose of BG9719 (0.1 mg/kg IV). In FIG. 11, the Baseline glomerular filtration rate (GFR) is shown. GFR is relatively normal after 1 and 2 days of furosemide dosing but decreases to about 60% of normal after 3 days of furosemide dosing.

Figure 12:
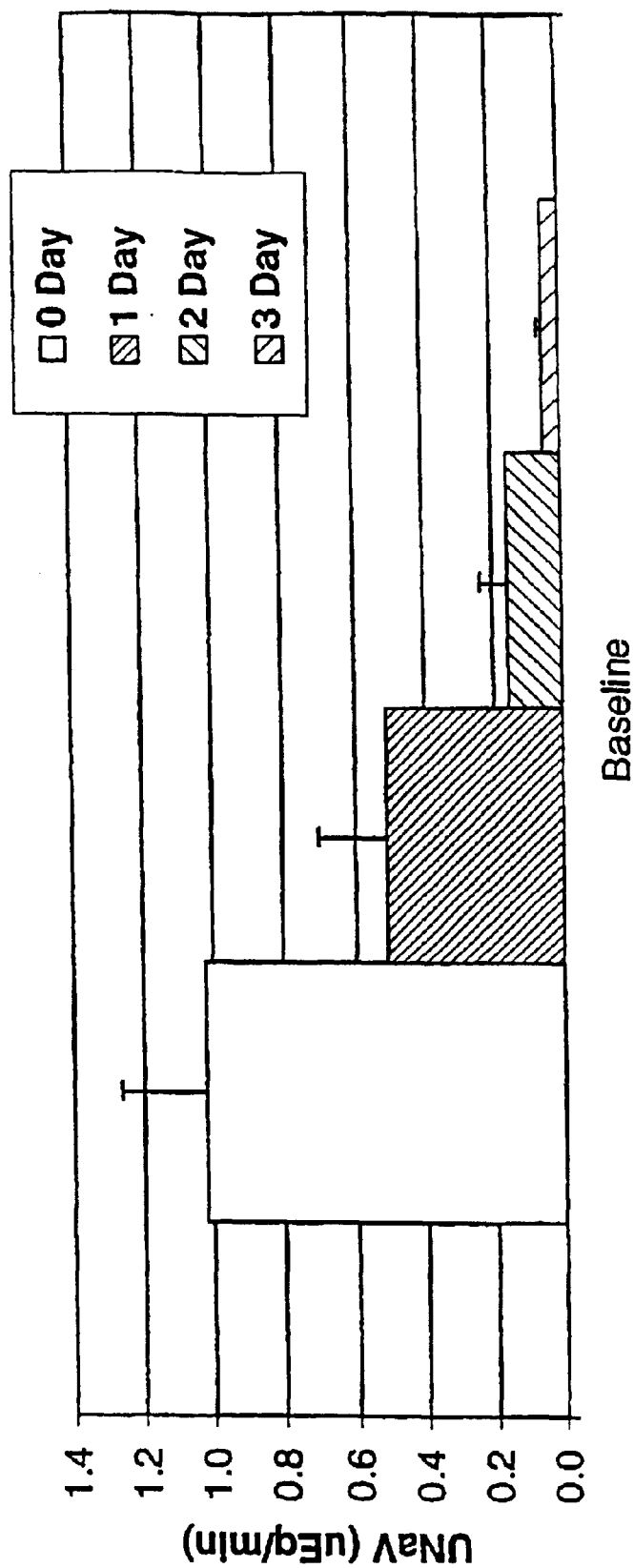
FIG. 12: These data are from the same rats in FIG. 11. We collected a 30 minute baseline urine and determined basal sodium excretion in these rats. These data are shown in this slide. Normally (Day 0 rats), the rats excrete about 0.6 uEq/min. After 1 day of furosemide, this is reduced to about 0.5 uEq/min. There is a further reduction after 2 and 3 days of furosemide—to a point where the rats are basically excreting no sodium.

FIG. 12 shows Baseline urinary sodium excretion (UNaV). Normal baseline sodium excretion is about 1 uEq/min in these rats (Day 0). This decreases substantially following 1 days dosing with furosemide and continues to decrease with 2 and 3 days of dosing. Thus, these rats are in a state of robust sodium retention.

Figure 13:
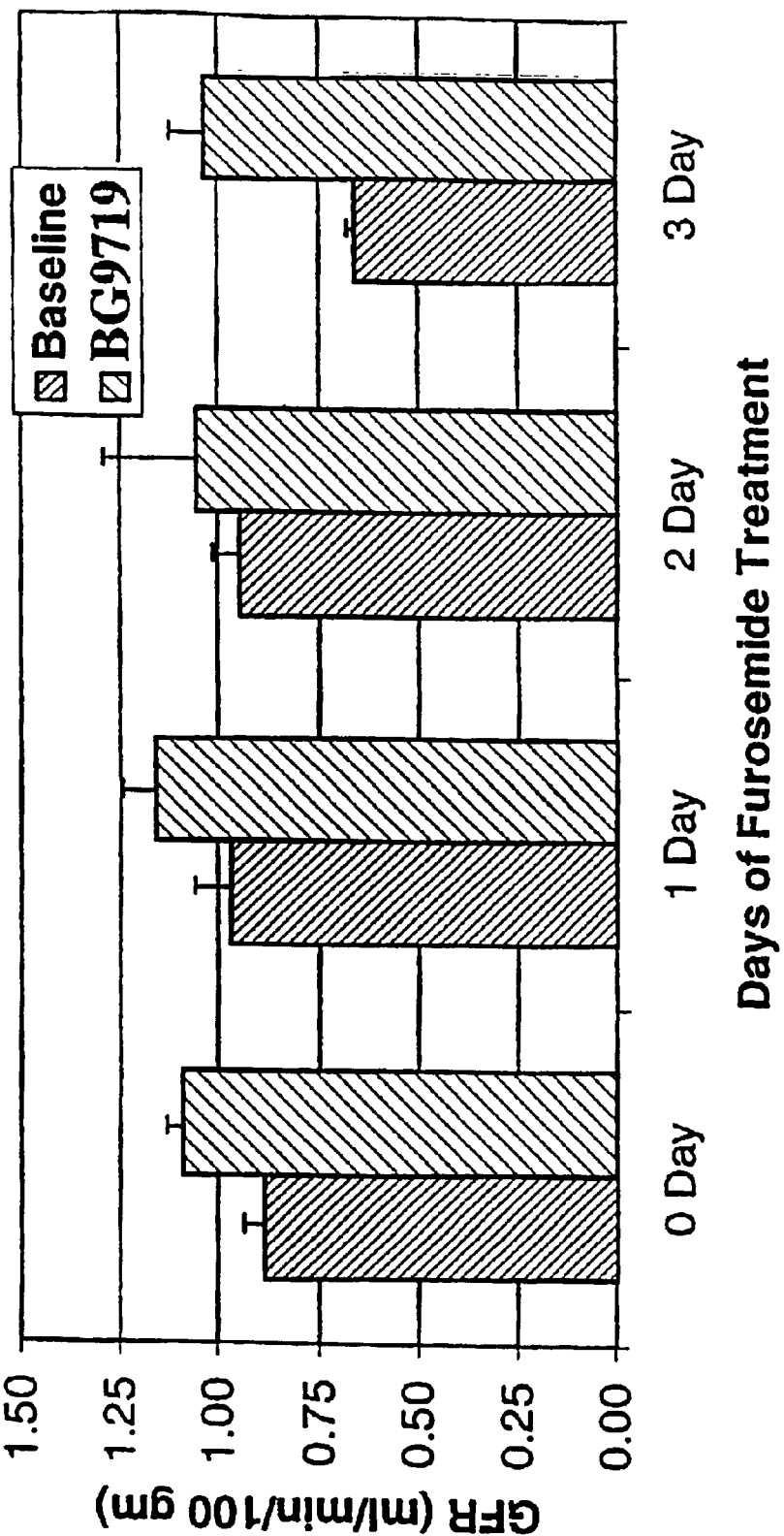
FIG. 13: This is a re-plot of FIG. 11, in terms of baseline GFR's (solid bars). Additionally the GFR from the 30 minute post-BG9719 urine collections have been added. BG9719 was dosed in these animals as 0.1 mg/kg IV (near maximal dose) after collection of the baseline urines.
Figure 14:
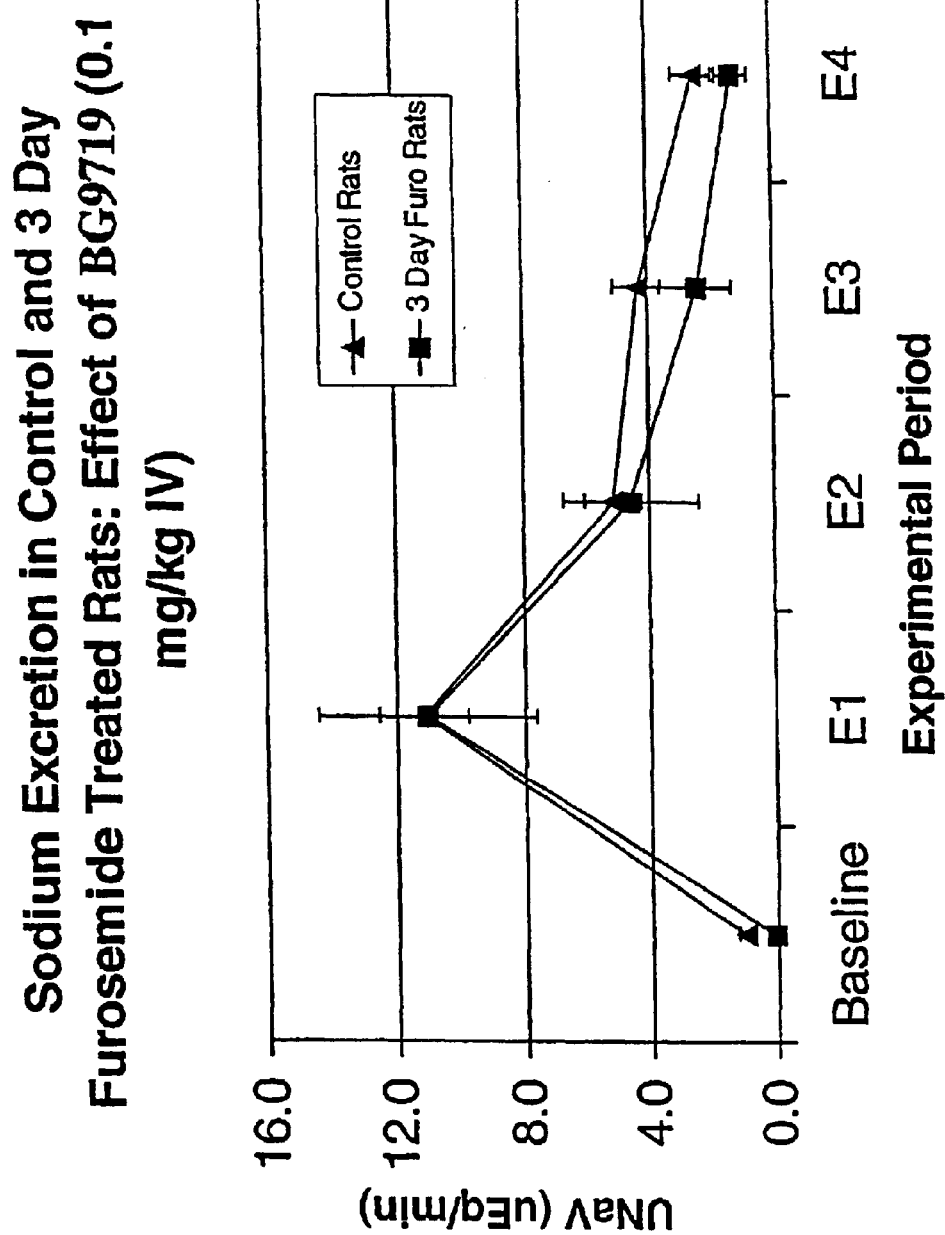
FIG. 14: shows the natriuretic response to BG9719 (0.1 mg/kg IV) in normal rats (Control Rats) and rats that have received 3 days of furosemide treatment. 'E1' is the first fifteen minute period after dosing, 'E2' is the next 15 minute period, while 'E3' and 'E4' are consecutive 30 minute periods following E2.

FIG. 13—Glomerular filtration rate (GFR) is shown at baseline and after dosing with BG9719. After receiving BG9719, GFR increases in all groups. Of note, the GFR in the Day 3 rats, which are decreased at baseline, recover to a level not different than normal rats. In FIG. 14—Urinary sodium excretion (UNaV) is shown for rats receiving no furosemide (Control Rats) and rats treated with furosemide for 3 days (3 Day Furo Rats). "E1" represents the first 15 minutes after dosing, "E2" is the second fifteen minute period, "E3" and "E4" are subsequent 30 minute periods. As shown, intravenous administration of BG9719 induces a natriuresis that reaches maximum within the first fifteen minutes and then decreases back toward baseline thereafter. The response is the same between control rats and rats treated with 3 days of furosemide dosing.

EXAMPLE 8

Figure 10:
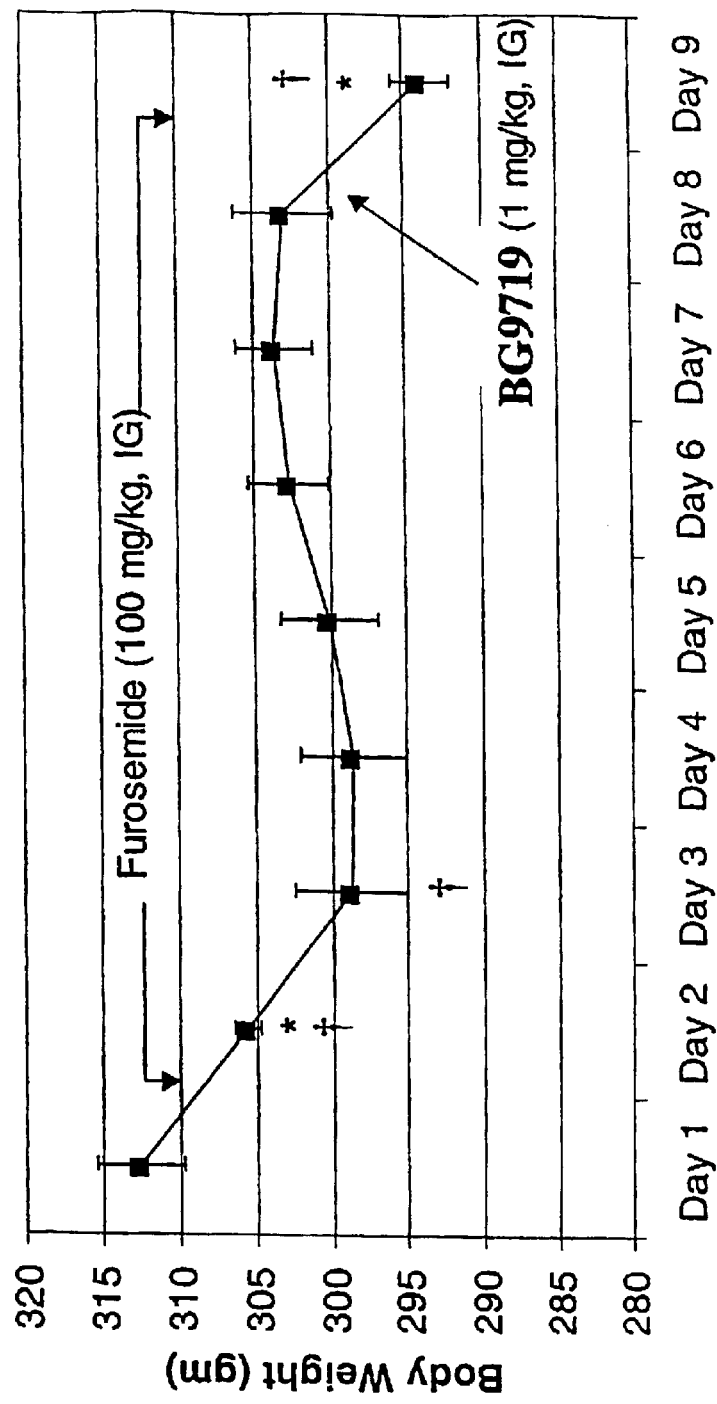
FIG. 10: furosemide dosing induces a significant reduction in body weight after one and two days of dosing.

Six male Sprague-Dawley rats received once daily dosing with furosemide (100 mg/kg by gavage) for seven days. On the eighth day, they received a combination dose of furosemide (100 mg/kg) and BG9719 (1 mg/kg), by gavage. Body weights were measured prior to each days dosing and twenty-four hours after the combination dose. As shown in FIG. 10, furosemide dosing induces a significant reduction in body weight after one and two days of dosing. Thereafter, there is no further reduction in weight. However, if BG9719 is then co-administered with furosemide, an additional, significant reduction in body weight is observed.

EXAMPLE 9

Figure 15:
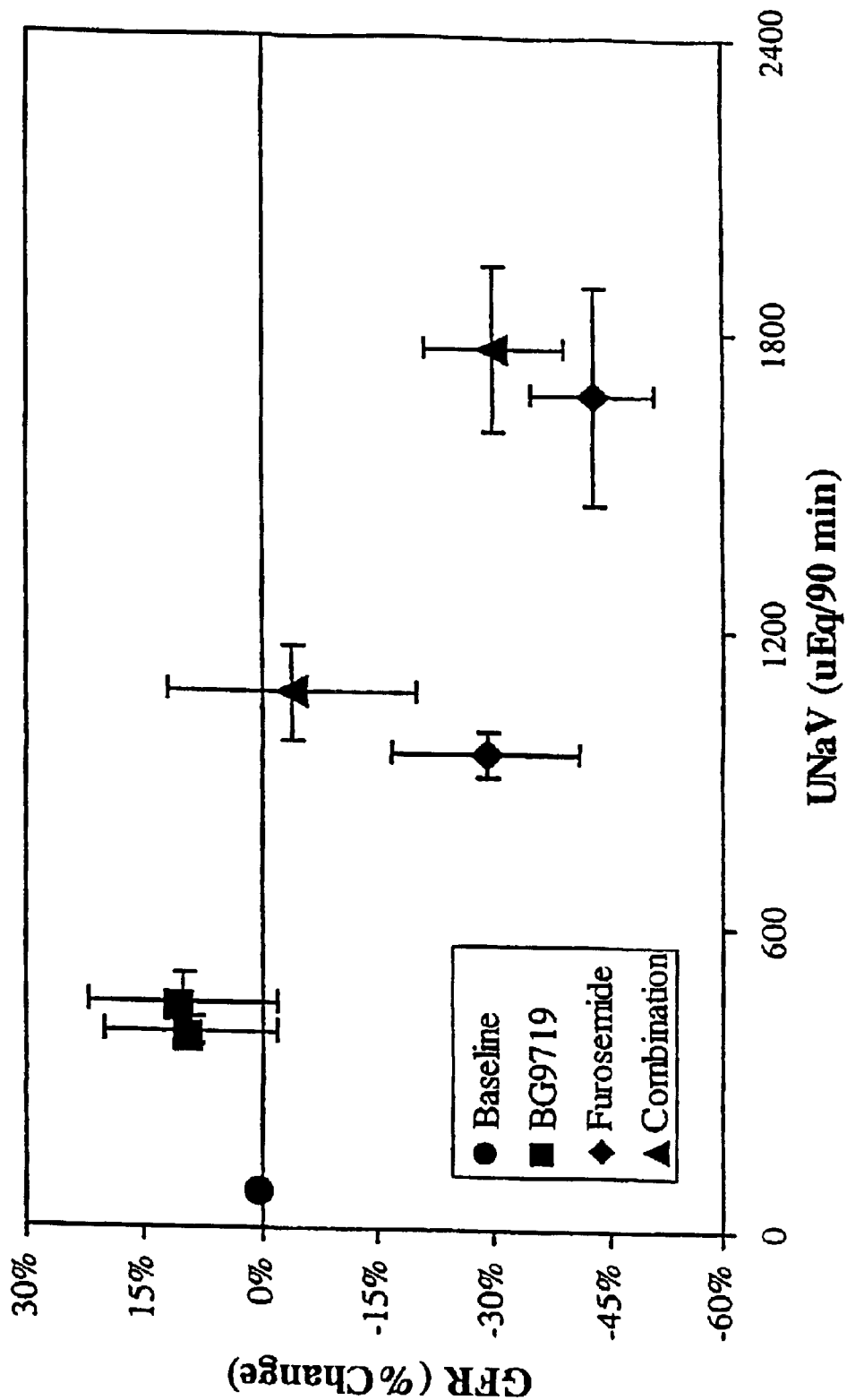
FIG. 15: Is a graph of the natriuretic response, expressed as total sodium excreted in the 90 minutes after dosing, versus the change in glomerular filtration rate, expressed as a percent change from baseline.

Male Sprague-Dawley rats were anesthetized and instrumented to measure renal function. Insulin was infused intravenously and concentrations of insulin in plasma and urine were determined by a biochemical assay. The urinary clearance of insulin was used as a measure of glomerular filtration rate. Urine was collected via an implanted bladder catheter. Urine volumes were determined gravimetrically and urinary sodium concentration was measured by flame photometry. Sodium excretion (UNaV; uEq/hr) was calculated from these values. Following a baseline collection period, rats received a single intravenous bolus dose of either BG9719 (0.03 mg/kg or 0.1 mg/kg), furosemide (10 mg/kg or 100 mg/kg) or a combination of furosemide (10 mg/kg or 100 mg/kg) and BG9719 (0.1 mg/kg). Shown in FIG. 15 is a graph of the natriuretic response, expressed as total sodium excreted in the 90 minutes after dosing, versus the change in glomerular filtration rate, expressed as a percent change from baseline. As shown, the two doses of BG9719 increased sodium excretion to similar levels and increased GFR. Furosemide dose-dependently increased natriuresis. However, the increased natriuresis was at the expense of decreased renal function, as assess by a reduction in GFR. When BG9719 was co-administered with furosemide, the natriuretic response was increased and the reduction in GFR was attenuated.

What is claimed is:

1. A method of inducing a diuretic effect in a mammal, comprising administration of a therapeutically effective amount of BG9719, or salts or esters thereof in combination with a non-adenosine modifying diuretic.

2. The method of claim 1, wherein a therapeutically effective amount of BG9719, or salts or esters thereof, is administered in combination with a non-adenosine modifying diuretic chosen from the group consisting of hydrochlorothiazides, furosemide, torsumide, bumetanide, thacrynic acid, piretanide, norsemide, spironolactone, triamterene, and amiloridethiazides.

3. The method of claim 2, wherein the non-adenosine modifying diuretic is furosemide.

4. The method of claim 3, wherein the furosemide is administered before BG9719.

5. The method of claim 3, wherein the furosemide is administered after BG9719.

6. The method of claim 3, wherein the furosemide is administered substantially simultaneously with BG9719.

7. The method of claim 2, wherein the mammal is refractory to a diuretic.

8. A method of maintaining or restoring the diuretic effect of a non-adenosine modifying diuretic in a patient comprising the administration of a therapeutically effective amount of BG9719, or salts or esters thereof, in combination with said non-adenosine modifying diuretic.

9. The method of claim 8, wherein the non-adenosine modifying diuretic is chosen from the group consisting of hydrochlorothiazides, furosemide, torsumide, bumetanide, thacrynic acid, piretanide, norsemide, spironolactone, triamterene, and amiloridethiazides.

10. The method of claim 9, wherein the non-adenosine modifying diuretic is furosemide.

11. The method of claim 10, wherein the furosemide is administered before BG9719.

12. The method of claim 10, wherein the furosemide is administered after BG9719.

13. The method of claim 10, wherein the furosemide is administered substantially simultaneously with BG9719.

14. A method of maintaining or restoring renal function in a patient comprising the step of administering a therapeutically effective amount of BG9719, or salts or esters thereof, in combination with a non-adenosine modifying diuretic.

15. The method of claim 14, wherein the non-adenosine modifying diuretic is chosen from the group consisting of hydrochlorothiazides, furosemide, torsumide, bumetanide, thacrynic acid, piretanide, norsemide, spironolactone, triamterene, and amiloridethiazides.

16. The method of claim 15, wherein the non-adenosine modifying diuretic is furosemide.

17. The method of claim 16, wherein the furosemide is administered before BG9719.

18. The method of claim 16, wherein the furosemide is administered after BG9719.

19. The method of claim 16, wherein the furosemide is administered substantially simultaneously with BG9719.

* * * * *